United States Patent [19]

Hilpert

[11] Patent Number: 5,670,653
[45] Date of Patent: Sep. 23, 1997

[54] PROCESS FOR THE MANUFACTURE OF (4,5)-TRANS-OXAZOLIDINES

[75] Inventor: Hans Hilpert, Reinach, Switzerland

[73] Assignee: Hoffmann-La Roche Inc., Nutley, N.J.

[21] Appl. No.: 739,565

[22] Filed: Oct. 30, 1996

[30] Foreign Application Priority Data

Nov. 6, 1995 [CH] Switzerland ............... 03131/95

[51] Int. Cl.$^6$ ................................ C07D 263/20
[52] U.S. Cl. ........................... 548/229; 548/230
[58] Field of Search ............................ 548/229, 230

[56] References Cited

U.S. PATENT DOCUMENTS 5,495,025 2/1996 Hilpert ........................ 548/477

FOREIGN PATENT DOCUMENTS 0 635 493 1/1995 European Pat. Off. .

OTHER PUBLICATIONS

Matsumoto, et al, A Steroselective Synthesis Of Cyclohexylnorstatine, The Key Component Of A Renin Inhibitor, Tetrahedron Letters, vol. 31, No. 29, pp 4175–4176 (1990).

Kobayashi, et al, Novel Synthesis Of Three Types of C–Terminal Components Of Renin Inhibitors From Unnatural (2S,3S)–Tartaric Acid, Chem. Pharm. Bull. vol. 39, No. 10, pp. 2550–2555 (1991).

Melon et al, Enantiomerically pure 3–amino–2–hydroxy and 5–amino–4–hydroxy acids from D–isoascorbic acid, Bull. Soc. Chim. Fr. vol. 129, p. 585–592, 1992.

Herranz et al, An Improved One–Pot Method for the Stereoselective Synthesis of the (2S,3R)–3–Amino–2–hydroxy Acids: Key Intermediates for Bestatin and Amastatin, J. Org. Chem. vol. 55, pp. 2232–2234, 1990.

Patel et al, Activated Ketone Based Inhibitors of Human Renin, Journal of Medicinal Chemistry, vol. 36, No. 17, pp. 2431–2447, 1993.

Magnus et al, New Strategy for the Synthesis of the Taxane Diterpenes:Formation of the A–Ring via Nitro–aldol and Aldol Reactions, J. Chem. Soc., Chem. Commun., pp. 1933–1934, 1995.

Iizuka et al, Orally Potent Human Renin Inhibitors from Angiotensinogen Transition State: Design, Synthesis, and Mode of Interaction, J. Med. Chem. vol. 33, pp. 2707–2714, 1990.

Primary Examiner—Johann Richter
Assistant Examiner—Jane C. Oswecki
Attorney, Agent, or Firm—George W. Johnston; William H. Epstein; Lewis J. Kreisler

[57] ABSTRACT

Compounds containing a (4,5)-cis-2-oxo-oxazolidine ring are isomerized to the corresponding (4,5)-trans-2-oxo-oxazolidine by treating the cis compound with a strong base.

14 Claims, No Drawings

PROCESS FOR THE MANUFACTURE OF (4,5)-TRANS-OXAZOLIDINES

FIELD OF THE INVENTION

The present invention relates to a novel process for the manufacture of (4,5)-trans-oxazolidines from the corresponding cis compounds.

BACKGROUND OF THE INVENTION

These compounds are important intermediates for the manufacture of β-aminocarboxylic acid derivatives which are building bricks for pharmacologically active substances, especially those which are suitable for the treatment of viral infections, for lowering blood pressure and for the control of tumors. Some uses for (4,5)-trans-oxazolidines are summarized for example in Melon et al. (1992), Bull. Soc. Chim. Fr., 129, 585–593. The compounds of the present invention are useful for the synthesis of renin inhibitors, bestatin, amastatin and HIV-1 protease inhibitors.

Herranz et al. (J. Org. Chem. (1990) 55, 2232–2234) describe a synthesis of (2S,3R)-3-amino-2-hydroxyphenylbutyric acid esters using a trimethylsilyl-protected cyanohydrin for the production of bestatin and amastatin.

Patel et al. (J. Med. Chem. (1993) 36, 2431–2447) describe the preparation of renin inhibitors based on activated ketones. In the synthesis of the 2-oxo-oxazolidine intermediates an expensive working-up of the corresponding precursors by chromatography and crystallization is required.

Further synthetic routes for the preparation of (4,5)-trans-2-oxo-oxazolidines are described, for example, by Melon et el. (Bull. Soc. Chim. Fr. (1992) 129, 585–593).

SUMMARY OF THE INVENTION

In accordance with this invention, any compound containing a (4,5)-cis-2-oxo-oxazolidine ring is isomerized to the corresponding (4,5)-trans-2-oxo-oxazolidine-containing compound by a process comprising treating the (4,5)-cis compound with a strong base to give the (4,5)-trans compound.

It has now surprisingly been found that the process of the present invention yields the trans-configurated 2-oxo-oxazolidines with high stereoselectivity. The process in accordance with the invention comprises converting a (4,5)-cis-2-oxo-oxazolidinone into the corresponding (4,5)-trans-2-oxo-oxazolidinone by means of a strong base.

Specific embodiments of this invention involve the isomerization of (4,5)-cis-2-oxo-oxazolidines of formula (II)

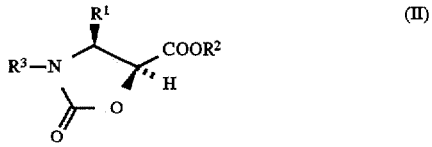

wherein $R^1$ is isobutyl or benzyl;

$R^2$ is any acid protecting group, preferably alkyl; and $R^3$ is any amino protecting group, preferably an amine, amide or urethane protecting group; or hydrogen, comprising treating compounds of formula (II) with a strong base to give compounds of formula (I)

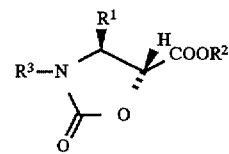

in which $R^1$, $R^2$ and $R^3$ in formula (I) are as defined above.

DETAILED DESCRIPTION OF THE INVENTION

In accordance with this invention, any compound which contains a (4,5)-cis-2-oxo-oxazolidine moiety can be isomerized to provide the corresponding (4,5)-trans bond. This process is an important new method for producing a (4,5)-trans-2-oxo-oxazolidine moiety. These compounds are important in the field since they can be intermediates for anticancer, antiviral and antimicrobial agents. For instance, compounds of formula II can be converted to compounds of formula I, which are known intermediates for producing pharmaceutically active agents as disclosed in Magnus and Pye (J. Chem. Soc., Chem. Commun., (1995) 1933–1934); U.S. Pat. No. 5,495,025 and Herranz et al. (J. Org. Chem. (1990) 55, 2232–2234). Magnus and Pye (J. Chem. Soc.) describe a reaction sequence for the manufacture of taxol derivatives. Here, the taxol side-chain on ring system A can be introduced by simple esterification with the compounds in accordance with the invention, with the correct stereochemistry being obtained in one reaction step. U.S. Pat. No. 5,495,025 describes the synthesis of 2-[3(S)-amino-2(R)-hydroxy-4-phenylbutyl]-N-tert.butyl-decahydro-(4aS,8aS)-isoquinoline-3(S)-carboxamide, which is useful as an intermediate in the chemical synthesis of certain anti-retroviral compounds. Herranz et al. (J. Org. Chem. (1990) 55, 2232–2234 describe the synthesis of (2S,3R)-3-amino-2-hydroxy acids, which are intermediates for the aminopeptidase inhibitors Bestatin and Amastatin, which possess antitumor and antimicrobial activities.

Please note U.S. Pat. No. 5,495,025, European Patent Publication No. EP 0635493, and Herranz, et al. (J. Org. Chem. (1990) 55, 2232–2234. Thus, cis-2-oxo-oxazolidines can be prepared, for example, by reacting an α-hydroxy-β-aminoacid ester with a corresponding carbonylating agent. Examples of carbonylating agents include esters of haloformic acids (phenylchloroformate), carbonyldiimidazole, phosgene, and triphosgene. Cis-2-oxo-oxazolidines are used, for example, in the synthesis of HIV protease inhibitors.

Preferred processes are those in which (4,5)-cis-2-oxo-oxazolidines of formula (II) above in which $R^2$ is lower-alkyl and $R^3$ is hydrogen or a benzyl, benzoyl, acetyl or allyl group are isomerized. Especially preferred processes are those in which (4,5)-cis-2-oxo-oxazolidines of formula (II) above in which $R^2$ is lower-alkyl and $R^3$ is hydrogen are isomerized.

In carrying out the issomerization process of this invention, temperature is not critical. The reaction isomerization is conveniently carried out at a preferred temperature between −20° C. and +80° C., most preferably between +20° C. and +45° C.

In carrying out the isomerization process of this invention, any conventional strong base can be utilized. Among the preferred strong bases are alkali metal or alkaline earth metal alcoholates, i.e. alcoholates in which the hydrocarbon chain comprises alkyl groups as set forth for $R^2$, lithium, sodium or potassium amide, alkyllithium compounds or alkylmagnesium halides. Sodium methylate or potassium tert.butylate is preferred. Numerous bases as well as their relative strengths are available in standard treatises and handbooks. Accordingly, other bases suitable for isomerizing cis-2-oxo-oxazolidines to the trans configuration are readily recognized or determined by those of skill in the art.

The process is carried out in any conventional inert solvent, which will be familiar to any person skilled in the art. The term "inert solvent" refers to a solvent which is inert under the described reaction conditions. For example, solvents such as toluene, tetrahydrofuran (THF) or alcohols corresponding to the groups $R^2$, etc. can be used.

In the specific oxazolidine of formula II, $R^2$ can be any conventional organic acid protecting group. These conventional acid protecting groups can be removed at a later stage in the synthesis of pharmaceutically active compounds by methods well known in the art, including acid hydrolysis and catalytic hydrogenation. The preferred organic acid protecting groups are the esters. Any conventional ester that can be hydrolyzed to yield the acid can be utilized as the protecting group. Exemplary esters useful for this purpose are the lower alkyl esters, particularly methyl and ethyl ester, the aryl esters, particularly phenyl ester and the aryl lower alkyl esters, particularly benzyl ester.

The term "alkyl" alone or in combination relates to a cyclic, branched or straight-chain monovalent hydrocarbon group containing one to twenty four, preferably one to twelve, carbon atoms. The term "lower-alkyl" is concerned with straight-chain or branched saturated alkyl groups with 1 to 8, preferably 1–4, carbon atoms such as methyl, ethyl, n-propyl, isopropyl, n-butyl, isobutyl, sec.butyl, tert.butyl, pentyl, hexyl, heptyl, octyl and the like.

Alkyl and lower-alkyl groups can optionally carry one or more substituents selected from alkyl, alkoxy, lower-alkyl, halogen, hydroxy, amino, nitro, thio and the like.

The term "halogen" stands for fluorine, chlorine, bromine or iodine.

In the specific oxazolidine of formula II, when $R^2$ is an amino protecting group, any conventional amino protecting group can be utilized. These conventional amino protecting groups can be removed by methods well known in the art, including acid hydrolysis and catalytic hydrogenation. These conventional amino protecting groups include lower alkyl carbonyl, aryloxycarbonyl, halo substituted lower alkoxy carbonyl and arylloweralkoxycarbonyl, for example benzyloxycarbonyl, t-butoxycarbonyl, etc. Amine, amide or urethane protecting groups embrace groups such as, for example, benzyl, benzoyl, allyl, acetyl or tert.butoxycarbonyl.

Where required, isolation and purification of the compounds obtained according to the process in accordance with the invention can be carried out using any suitable separation or purification method, for example by filtration, extraction, crystallization, column chromatography, preparative HPLC, thin-layer chromatography or combinations of these or other procedures which are known from the state of the art.

This invention will be better understood by reference to the following Examples. These examples are intended to illustrate the invention only, and should not be construed to limit in any way the invention which is defined in the claims which follow.

EXAMPLE 1

Manufacture of methyl (4S,5R)-4-benzyl-2-oxo-oxazolidine-5-carboxylate

A solution of 70.0 g of a 92:8 mixture of the (4S,5S)- and (4S,5R)-isomers of methyl 4-benzyl-2-oxo-oxazolidine-5-carboxylate and 7.0 g of potassium tert.butylate in 700 ml of THF was stirred at 20° C. for four hours and at 45° C. for 2 hours, the solution was washed twice with semi-saturated sodium chloride solution, dried over $MgSO_4$, filtered and the filtrate was evaporated to give 68 g (97%) of 95% methyl (4S,5R)-4-benzyl-2-oxo-oxazolidine-5-carboxylate (tlc ($SiO_2$, ethyl acetate):$R_f$=0.5).

EXAMPLE 2

Manufacture of methyl (4S,5R)-4-cyclohexylmethyl-2-oxo-oxazolidine-5-carboxylate For the manufacture of the aforementioned compound, methyl (4S,5S)-4-cyclohexylmethyl-2-oxo-oxazolidine-5-carboxylate, obtainable by hydrogenating methyl (4S,5R)-4-benzyl-2-oxo-oxazolidine-5-carboxylate, is reacted under the conditions given in Example 1. Methyl (4S,5R)-4-cyclohexylmethyl-2-oxo-oxazolidine-5-carboxylate is obtained in a yield of about 95%.

What is claimed is:

1. A process for isomerizing a compound containing a (4,5)-cis-2-oxo-oxazolidine ring to the corresponding compound containing a (4,5)-trans-2-oxo-oxazolidine ring, comprising treating the (4,5)-cis compound with a strong base to give the (4,5)-trans compound.

2. A process for producing (4,5)-trans-2-oxo-oxazolidines, which process comprises treating a (4,5)-cis-2-oxo-oxazolidine of the structure:

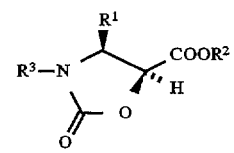

wherein
$R^1$ is benzyl or isobutyl,
$R^2$ is an acid protecting group; and
$R^3$ is an amino protecting group,
with a strong base to give a (4,5)-trans-2-oxo-oxazolidine of the structure:

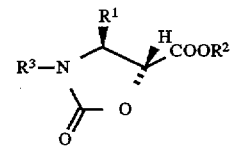

3. The process according to claim 2, wherein the amino protecting group is an amine, an amide, or a urethane.

4. The process according to claim 2, wherein the acid protecting group is an alkyl group.

5. The process according to claim 2, wherein $R^2$ is a lower-alkyl group and $R^3$ is hydrogen or a benzyl, benzoyl, acetyl or allyl group.

6. The process according to claim 5, wherein $R^3$ is hydrogen.

7. The process according to claim 2, wherein $R^1$ is isobutyl.

8. The process according to claim 2, wherein $R^1$ is benzyl.

9. The process according to claim 2, wherein the strong base is an alkali metal alcoholate, an alkaline earth metal alcoholate, a lithium amide, a sodium amide, a potassium amide, an alkyllithium compound, or an alkylmagnesium halide.

10. The process according to claim 2, wherein the strong base is sodium methylate or potassium tert.butylate.

11. The process according to claim 2, wherein the treating with the strong base is carried out at a temperature of −20° C. to +80° C.

12. The process according to claim 11, wherein the temperature is +20° C. to +45° C.

13. The process according to claim 2, wherein the treatment is carried out in the presence of a solvent selected from the group consisting of toluene, tetrahydrofuran and an alcohol.

14. The process according to claim 2, wherein the (4,5)-cis-2-oxo-oxazolidine is present in a mixture with its corresponding (4,5)-trans-2-oxo-oxazolidine at the start of the treatment.

* * * * *